United States Patent [19]

Isenberg

[11] 4,151,060
[45] Apr. 24, 1979

[54] SOLID STATE FILTER FOR GAS SENSORS

[75] Inventor: Arnold O. Isenberg, Pittsburgh, Pa.

[73] Assignee: Westinghouse Electric Corp., Pittsburgh, Pa.

[21] Appl. No.: 874,186

[22] Filed: Feb. 1, 1978

[51] Int. Cl.² .................................. G01N 27/46
[52] U.S. Cl. ............................. 204/195 S; 55/16; 55/68; 55/158; 55/523; 423/579
[58] Field of Search ............................ 204/15, 195 S; 429/30–33, 193, 101, 104; 423/579; 55/16, 68, 158, 523

[56] References Cited

U.S. PATENT DOCUMENTS

| Re. 28,792 | 4/1976 | Ruka et al. | 204/195 S |
|---|---|---|---|
| 3,410,728 | 11/1968 | Fullman et al. | 429/33 |
| 3,438,241 | 4/1969 | McKinley | 73/23 |
| 3,445,293 | 5/1969 | White | 429/33 |
| 3,579,292 | 5/1971 | Mullhaupt et al. | 423/579 |
| 3,597,169 | 8/1971 | Savage | 423/579 |
| 3,720,594 | 3/1973 | Wilson | 204/195 S |
| 3,791,937 | 2/1974 | Besson et al. | 204/195 S |
| 3,835,012 | 9/1974 | Hemak | 204/195 S |
| 3,841,987 | 10/1974 | Friese et al. | 204/195 S |
| 3,847,672 | 11/1974 | Trocciola et al. | 55/158 |
| 3,874,899 | 4/1975 | Miszenti et al. | 55/523 |
| 3,928,161 | 12/1975 | Friese et al. | 204/195 S |
| 3,974,054 | 8/1976 | Poolman et al. | 204/195 S |
| 3,977,830 | 8/1976 | Topol | 204/195 S |
| 3,980,763 | 9/1976 | Mullhaupt | 423/579 |
| 4,021,326 | 5/1977 | Pollner et al. | 204/195 S |
| 4,040,930 | 8/1977 | Dillon | 204/195 S |

Primary Examiner—T. Tung
Attorney, Agent, or Firm—M. P. Lynch

[57] ABSTRACT

A mixed-conducting (electronic-ionic) membrane exhibiting substantially no mechanical porosity, is employed as a solid state filter in combination with a gas sensor to protect the gas sensor from deterioration and contamination by particulate and certain gaseous matter present in the gas environment being monitored.

5 Claims, 1 Drawing Figure

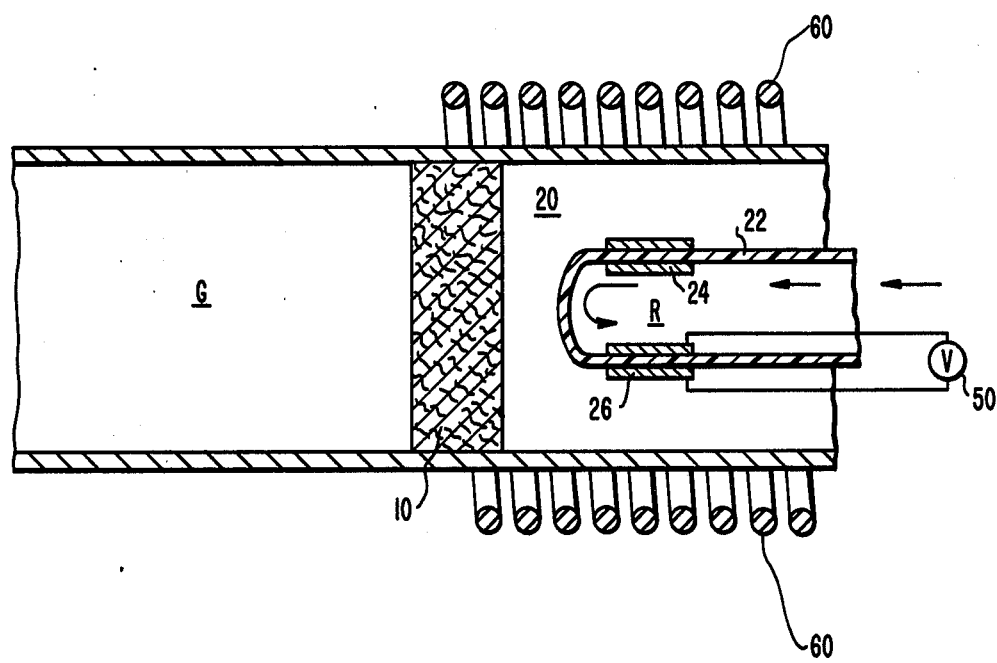

SOLID STATE FILTER FOR GAS SENSORS

BACKGROUND OF THE INVENTION

The in situ sensing of gas species in industrial heating and firing operations, especially in the steel making process and cement kiln operation, is made difficult by the presence of large amounts of particulate matter that tend to clog or penetrate mechanical filters employed in combination with gas sensors. Similarly, gaseous metal compounds and sulfur species can cause rapid sensor electrode deterioration.

SUMMARY OF THE INVENTION

There is disclosed herein with reference to the accompanying drawing an electrochemical filter exhibiting significant oxygen ion conductivity and essentially no mechanical porosity functioning as a filter in combination with an oxygen gas sensor to isolate the oxygen gas sensor from damaging contact by particulate matter in an oxygen containing industrial environment while maintaining the oxygen gas concentration constant on both sides of the filter. The industrial gas environment is therefore sensed with respect to oxygen by eliminating other gaseous and particulate matter.

DESCRIPTION OF THE DRAWINGS

The invention will become more readily apparent from the following exemplary description in connection with the accompanying schematic illustration of the preferred embodiment of the invention.

DESCRIPTION OF THE PREFERRED EMBODIMENT

Referring to the drawing, there is schematically illustrated an electrochemical filter 10 positioned to isolate the oxygen sensor 20 from gaseous and particulate matter present in the industrial gas environment G while supporting oxygen ion conductivity to transfer the oxygen present in the industrial gas environment G to the oxygen gas sensor 20. The oxygen gas sensor 20 develops an EMF signal at elevated temperatures which is indicative of the oxygen content of the industrial gas environment G which is measured by voltmeter 50.

The oxygen gas sensor 20 is typically illustrated as a solid electrolyte electrochemical cell consisting of a tubular solid electrolyte member 22 having an inner electrode 24 and an outer electrode 26 disposed in intimate contact with the solid electrolyte member 22. A stable oxygen reference environment R, such as air, is provided within the tubular electrolyte member 22 and in contact with the inner electrode 24 which functions as an oxygen reference electrode. The oxygen transmitted by the electrochemical filter 10 from the industrial gas environment G contacts the external electrode 26 which functions as the sensing electrode. The differential oxygen pressure present between the electrodes 24 and 26 results in the generation of the EMF signal which is measured by the voltmeter 50 as an indication of the oxygen content of industrial gas environment G. The implementatiion and operation of the solid electrolyte electrochemical oxygen sensing cell 20 is described in detail in U.S. Pat. Nos. 3,347,767; 3,546,086 and U.S. Pat. Re. 28,792, all of which have been assigned to the assignee of the present invention and are incorporated herein by reference.

In contrast to the conventional filters which rely on mechanical porosity for the transfer of the oxygen from a gas environment to a protected gas sensor, such as described in U.S. Pat. No. 3,928,161 which is assigned to the assignee of the present invention, the electrochemical filter 10 has substantially no mechanical porosity, and instead, relies on the oxygen ionic and electronic conductivity capability of the electrochemical filter 10 to transfer the oxygen from the industrial gas environment G to the oxygen gas sensor 20. The electrochemcial filter 10 consists of a mixed conductor exhibiting both electronic and oxygen ionic conductivity which, when maintained at a sufficiently high temperature by the heater 60, supports substantial oxygen ion migration from the industrial gas environment G to the sensing electrode 26 of the oxygen gas sensor 20. The mixed oxide composition of the electrochemical filter 10 is such as to support only oxygen ion conductivity and electronic charge carriers, thereby filtering or isolating the oxygen gas sensor 20 from not only particulate matter in the industrial gas environment G, but from all other gas species other than oxygen. A typical mixed oxide composition suitable for functioning as the electrochemical filter 10 consists of a cermet, such as a mixture of platinum with stabilized zirconia, or a metal oxide doped zirconia exhibiting electronic as well as oxygen ion conductivity. Zirconia can be replaced with other suitable materials, such as ceria, thoria, hafnia, magnesia or mixed oxides comprised of mixtures of rare earth oxides with chromium, titanium, nickel and cobalt oxide. The basic criteria for a suitable electrochemical filter for use in combination with an oxygen sensor is good oxygen ion conductivity and sufficient electronic conductivity to establish oxygen transfer through the filter. The degree of electronic and anion conductivity determines the rate of response to a changing temperature. The higher the temperature, the faster the response. In the case of zirconia, a temperature over 700° C. is desirable and an electronic conduction that is within the same order of magnitude as the ionic conduction.

The composition of the filter 10 must maintain its mechanical integrity when exposed to the industrial gas envoronment G. The platinum-zirconia cermet represents such a stable material. Iron strontium oxide (FeSrO$_{3-x}$) represents another material that is stable at oxygen concentrations that exist in most firing operations.

Another useful electrochemical filter is an aluminum doped strontium titanate (SrTi$_{1-x}$Al$_x$O$_3$) wherein x is a number less than one. Ceria doped zirconia, uranium based mixed oxides or pure and rare earth doped uranium oxide fulfill the requirements for electrochemical filters that are operational down to very low, i.e., $10^{-15}$ atmospheres, oxygen concentrations. Oxide mixtures of praseodymium and nickel or cobalt, oxide mixtures of lanthanum and nickel, lanthanum and cobalt, and lanthanum and manganese are also very attractive candidates, especially in doped form that enhances electronic conduction. Dopants for this group of oxides are strontium, calcium and magnesium. The element lanthanum of this group of oxides can be replaced by cerium, praseodymium, neodymium and samarium; and the resulting mixed oxides will function in a similar manner as a solid state electrochemical filter.

I claim:

1. In an oxygen measuring apparatus including an oxygen ion conductive solid electrolyte electrochemical cell including a solid electrolyte member having a reference electrode disposed on one surface thereof and a sensing electrode disposed on an opposite surface thereof, and an oxygen reference media contacting said reference electrode wherein said electrochemical cell monitors the oxygen in a gas environment containing particulate matter and/or corrosive constituents which are potentially damaging to the solid electrolyte electrochemicial cell, the improvement for protecting said solid electrolyte electrochemical cell from potentially damaging particulate matter and corrosive constituents, the improvement comprising, a non-porous, solid-state filter means exhibiting sufficient electronic and oxygen ion conductivity to support the transfer of oxygen ions at elevated temperatures, said filter means being physically and operationally spaced apart from said solid electrolyte electrochemical cell and disposed between said monitored gas environment and said sensing electrode to isolate said cell from direct contact with the monitored gas environment, and means for heating said non-prous, solid-state filter means to cause said filter means to transfer oxygen from said monitored gas environment to the space between said filter means and said solid electrolyte electrochemical cell for contacting said sensing electrode, said solid electrolyte electrochemical cell developing an electrical signal indicative of the oxygen content of said monitored gas environment as a function of the oxygen present at said sensing electrode.

2. In the apparatus as claimed in claim 1 wherein said filter means is a cermet composition.

3. In the apparatus as claimed in claim 1 wherein said filter means is a mixed oxide composition for supporting oxygen ion and electronic conductivity.

4. In the apparatus as claimed in claim 2 wherein said cermet composition is a mixture of platinum and stabilized zirconia.

5. In the apparatus as claimed in claim 1 wherein said means for heating heats both said non-porous, solid-state filter means and said solid electrolyte electrochemical cell to a temperature to support the oxygen ion conductivity of said solid electrolyte electrochemical cell to generate said signal indicative of the oxygen content of said monitored gas environment, said operating temperature of said electrolyte electrochemical cell being substantially equivalent to the temperature of said filter means required to support the transfer of oxygen ions through said filter.

* * * * *